United States Patent
Herpin et al.

(10) Patent No.: US 7,368,158 B2
(45) Date of Patent: May 6, 2008

(54) ELASTOMERIC MEMBER PROVIDED WITH MONITORING MEANS

(75) Inventors: Gilles Herpin, Saint-Chamas (FR); Vincent Scala, Lancon de Provence (FR)

(73) Assignee: Eurocopter, Marignane (FR)

( * ) Notice: Subject to any disclaimer, the term of this patent is extended or adjusted under 35 U.S.C. 154(b) by 158 days.

(21) Appl. No.: 10/952,751

(22) Filed: Sep. 30, 2004

(65) Prior Publication Data
US 2005/0073111 A1    Apr. 7, 2005

(30) Foreign Application Priority Data
Oct. 3, 2003    (FR) .................................... 03 11591

(51) Int. Cl.
  B32B 3/00     (2006.01)
  B64C 27/35    (2006.01)
  B64C 27/51    (2006.01)
(52) U.S. Cl. ...................... 428/172; 416/107; 416/140; 267/141
(58) Field of Classification Search ................ 428/172, 428/187, 207; 416/107, 134 A, 140; 267/141, 267/141.1, 294
See application file for complete search history.

(56) References Cited

U.S. PATENT DOCUMENTS

| | | | | |
|---|---|---|---|---|
| 2,713,485 A | * | 7/1955 | Tillou ...................... | 267/141.1 |
| 3,619,533 A | * | 11/1971 | McFarland .................. | 200/308 |
| 4,003,265 A | * | 1/1977 | Craig et al. .................... | 74/5 R |
| 4,235,570 A | | 11/1980 | Ferris et al. | |
| 4,419,398 A | * | 12/1983 | Coffy et al. ................. | 428/174 |
| 4,676,669 A | * | 6/1987 | Byrnes et al. .............. | 384/221 |
| 5,601,408 A | | 2/1997 | Hunter et al. | |

FOREIGN PATENT DOCUMENTS

| FR | 2 378 975 | 8/1978 |
|---|---|---|
| FR | 2 497 173 | 7/1982 |

OTHER PUBLICATIONS

Plank R et al: "Automatisierte Risslangenmessung Bei Ermudungsrissausbreitung Untermixed-Mode-Beanspruchung" Technisches Messen TM, R. Oldenbourg Verlag. Munchen, DE, vol. 63, No. 2, Feb. 1, 1996, pp. 51-55, XP000554278 ISSN: 0171-8096 p. 51-54.

* cited by examiner

*Primary Examiner*—Donald Loney
(74) *Attorney, Agent, or Firm*—Young & Thompson

(57) ABSTRACT

The present invention relates to problems of maintenance of elastomeric members. According to the invention, the elastomeric member is provided with at least one elastomeric layer 1 disposed between two rigid strength members 2. In addition, the elastomeric member is provided with graduations 5 located on its visible surface 7, presenting an angle of inclination relative to the rigid strength members 2, thus making it possible to evaluate and monitor propagation of a crack 6 merely by inspecting it visually.

17 Claims, 1 Drawing Sheet

ELASTOMERIC MEMBER PROVIDED WITH MONITORING MEANS

The present invention relates to the maintenance of elastomeric members, as used in particular in laminated stops present in various hinge in the rotors of rotary wing aircraft.

BACKGROUND OF THE INVENTION

Amongst the members mentioned above, document FR 2 497 173, to which reference can be made for further details on this topic, discloses a laminated spherical stop for retaining and hinging a blade to the hub of a rotor for a rotary-wing aircraft. This stop comprises a central portion made up of a stack of alternating layers of flexible material, e.g. elastomer material, and rigid strength members in the form of spherical caps. The stack is arranged between an outer radial support secured to the hub, where "outer" is relative to the axis of the rotor, and inner radial support secured to the root portion of the corresponding blade.

More generally, the elastomeric member presents one of the following two structures. In a first embodiment, particularly suitable for the frequency adapters for a rotor of a rotary-wing aircraft, the elastomer layers are plane sheets, each bonded between two strength members in the form of plates. In a second embodiment, each elastomer layer is tubular and is bonded between an internal strength member and an external strength member which are likewise tubular.

In both cases, the elastomer is stressed in shear by the relative movement between two supports each fixed to a respective one of the two members of the rotor, i.e. to two adjacent blades or to a blade and the hub, between which relative lagging movements need to be damped.

When the elastomeric member is integrated in a laminated stop for retaining and hinging a blade on the hub of a rotor, the elastomer layers of the stop are stressed in shear by the lagging movements, and also by the pitch and flapping movements that are transmitted by the blade to the radially-inner support of the stop. In addition, the elastomer layers are also subjected to stress in compression by the centrifugal forces acting on the blade while the rotor is rotating. In operation, the elastomer is thus pressed dynamically at the frequency of rotation of the rotor, in flapping, in lagging, and above all in pitch.

The mechanical stresses exerted on the elastomer layers of the elastomeric member, regardless of the use to which it is put (laminated stop, frequency adapter, laminated spherical joint, etc.), can lead to cracks forming therein, parallel to the rigid strength members, which will lead in the end to the rigid strength members separating or to the elastomer splitting, and it is even possible for the elastomer to split into two portions. This drawback is particularly significant insofar as proper operation of the elastomeric member depends on good bonding between the various layers. Manufacturers of members of this type have consequently been led to set up separation criteria, based on the lengths of cracks that are visible from the outside, in order to determine when the time has come to replace a laminated stop that has cracks.

Measuring the lengths of cracks requires the use of tools, and in particular of a ruler. That method is particularly difficult to implement, given the generally difficult conditions of access to the elastomeric members because of the large number of components in the vicinity of said members, thereby considerably increasing the length of time required for maintenance operations.

OBJECT AND SUMMARY OF THE INVENTION

The object of the invention is to remedy those drawbacks by minimizing the tooling needed for measuring the lengths of cracks present in the visible surface of the elastomer member, while also reducing maintenance time and action.

In the context of the present invention, the visible surface is the surface that the operator can see while performing maintenance.

According to the invention, an elastomeric member is provided with at least one layer of flexible material disposed between two rigid strength members; in addition, and advantageously, said member is provided with graduations, located on the visible surface, and presenting an angle of inclination relative to said rigid strength members.

It is advantageous for the strong and inextensible material of the rigid strength members to be a metal or a reinforced plastics material, and for the flexible material to be an elastomer.

The graduations are advantageously constituted by one of the following elements:
  precut strips stuck onto the visible surface;
  lines of paint distributed over the visible surface, the paint possibly being made visible using a spectrum of specific frequencies (visible light, ultraviolet light, infrared light);
  color segments distributed over the visible surface;
  boss distributed over the visible surface; and
  notches formed in the visible surface.

In addition, it is useful for the set of graduations to be referenced so as to make it possible to ensure even more accurate checking of variations in the sizes of various cracks and their locations.

BRIEF DESCRIPTION OF THE DRAWINGS

The invention can be seen in greater detail from the following description on the basis of embodiments given purely by way of illustration, and with reference to the accompanying figures, in which.

MORE DETAILED DESCRIPTION

The elements present in both figures are given the same references in each of them.

Figure 1:
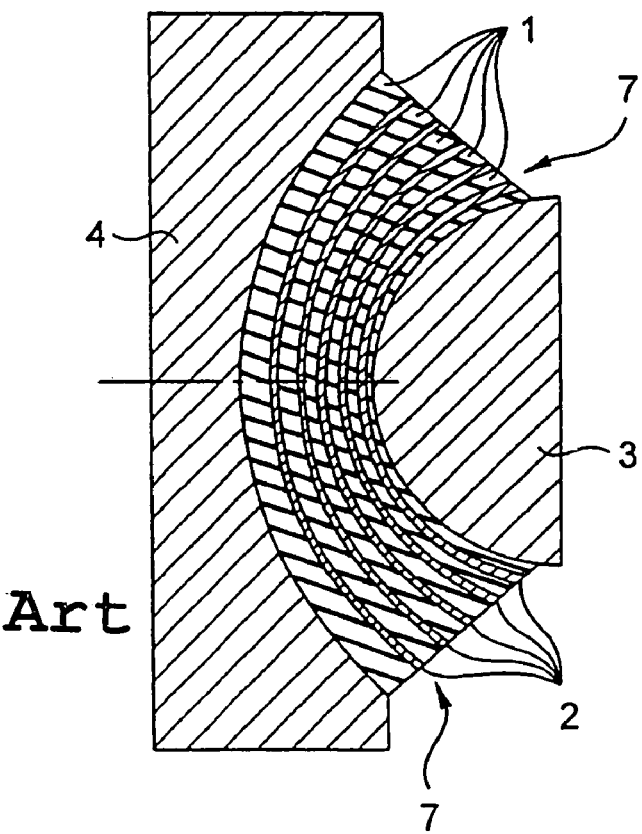
FIG. 1 is an axial section of a laminated stop of known type comprising an elastomeric member.

With reference to FIG. 1, a laminated stop of known type has an elastomeric member constituted by a stack of alternating elastomer layers 1 and rigid strength members 2 extending between an outer radial support 3 and an inner radial support 4.

Figure 2:
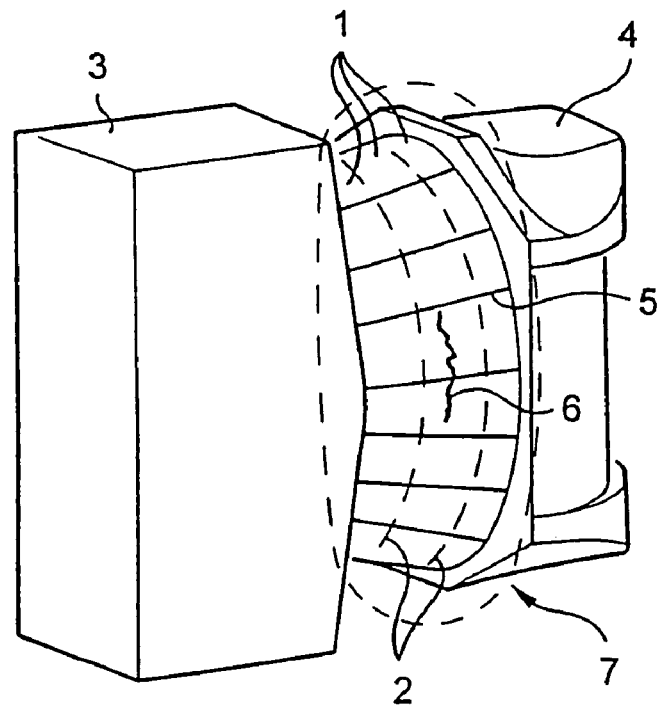
FIG. 2 is an isometric view of an elastomeric member mounted on a spherical stop, and including graduations on the visible surface of said member.

With reference to FIG. 2, an elastomeric member similar to the above-described member and mounted on a spherical stop includes the improvement of the invention. Graduations 5 can be seen on the visible surface 7 of the elastomeric member. The regular and quantified spacing between different graduations makes it possible, consequently, to evaluate the length of an observed crack 6. This type of marking which is present directly on the visible surface 7 has the advantage of considerably simplifying the time and operations required for maintenance since the extent of the crack 6 can be evaluated without tooling. Furthermore, since mere visible observation is sufficient for evaluating crack propagation, there is no need to remove the mechanical parts surrounding the elastomeric member, thereby reducing the number of operations that need to be performed.

In order to make the marking visible, various embodiments can be applied:

A first embodiment consists in graduating the elastomeric member by sticking precut strips onto the visible surface 7.

The second embodiment consists in graduating the elastomeric member by applying lines of paint on the visible surface 7.

The third embodiment consists in graduating the visible surface 7 by applying segments of color thereon. This embodiment has the advantage of making the detection of a crack 6 even more pertinent insofar as the graduations 5 can also serve as means for revealing optically whether the cracks are developing directly above a colored segment.

The fourth embodiment consists in graduating the elastomeric member by forming boss on the visible surface 7. In order to make this embodiment easier to implement, the boss may be integrated as recesses in the mold used for fabricating the elastomeric member.

The fifth embodiment consists in graduating the visible surface 7 by forming notches over the entire perimeter of the rigid strength members 2.

In addition, provision can be made to reference all of the graduations 5 present on the visible surface 7, e.g. numerically, so as to be even more accurate in tracking variation in the sizes of the various cracks 6 and their locations.

The various embodiments described above refer solely to an elastomer as a flexible material. Naturally, the invention also applies if the elastomer is replaced by any other flexible material.

Because the present invention is capable of numerous variations, modifications, and changes in details, some of which are specified explicitly above, it is envisaged that all of the subjects described in the present description and shown in the accompanying drawings should be interpreted as being illustrative and not limiting in any way. Consequently, it is clear that a device made in accordance with the concept of the present invention, and reasonably equivalent thereto, makes it possible to achieve the objects of the present invention and also significantly to improve the field relating to the maintenance of elastomeric members.

What is claimed is:

1. An aircraft stop comprising two supports and an elastomeric member extending between said two supports, said elastomeric member comprising at least one flexible layer disposed between two rigid strength members, said elastomeric member being provided with graduation marks, located on its visible surface and presenting an angle of inclination relative to said rigid strength members, said visible surface being a surface visible by an operator while performing maintenance on said aircraft, a space separating different graduation marks being regular and quantified so as to evaluate crack propagation in said flexible layer, said crack spanning between two of said graduation marks.

2. The aircraft stop according to claim 1, wherein said flexible layer is made of elastomer.

3. The aircraft stop according to claim 1, wherein the material of said rigid strength members is selected from the group comprising metals and reinforced plastics materials.

4. The aircraft stop according to claim 1, wherein the graduation marks are constituted by precut strips stuck onto said visible surface.

5. The aircraft stop according to claim 1, wherein the graduations are constituted by lines of paint on said visible surface.

6. The aircraft stop according to claim 1, wherein the graduation marks are constituted by segments of color distributed over said visible surface.

7. The aircraft stop according to claim 1, wherein the graduation marks consist in boss distributed over said visible surface.

8. The aircraft stop according to claim 1, wherein the graduation marks consist in notches formed in said visible surface.

9. The aircraft stop according to claim 1, wherein the graduation marks are referenced on the visible surface, in order to ensure even more accurate checking of variation in the various cracks and in their locations.

10. The aircraft stop according to claim 1, wherein said elastomeric member constitutes the central portion of a laminated stop arranged between said two supports, said two supports being an inner radial support and an outer radial support.

11. The aircraft stop according to claim 1, wherein said elastomeric member is integrated in a frequency adapter arranged between said two supports.

12. The aircraft stop according to claim 1, wherein said elastomeric member is integrated in a laminated spherical joint arranged between said two supports.

13. An aircraft laminated stop comprising an inner radial support, an outer radial support and an elastomeric member extending between said inner and outer radial supports, said elastomeric member comprising:

two rigid strength members; and at least one flexible layer disposed between said two rigid strength members, said elastomeric member having plural graduation lines on a surface that is visible to an operator servicing said aircraft, a spacing between said plural graduation lines being regular and quantified.

14. The aircraft laminated stop according to claim 13, wherein said at least one flexible layer is an elastomer.

15. The aircraft laminated stop according to claim 13, wherein said rigid strength members are selected from the group consisting of metals and reinforced plastics materials.

16. The aircraft laminated stop according to claim 13, wherein said elastomeric member is between two supports and said plural graduation lines extend from one of said two supports to another one of said two supports.

17. An aircraft laminated stop comprising an inner radial support, an outer radial support and an elastomeric member, said elastomeric member extending between said inner radial support and said outer radial support, said elastomeric member comprising at least one flexible layer laminated between two rigid strength members, said elastomeric member having plural graduation lines on a surface that is visible to an operator servicing said aircraft and being substantially perpendicular to a direction of lamination, said graduation lines spanning between and extending to said two supports.

\* \* \* \* \*